United States Patent [19]

Incorvia

[11] Patent Number: 4,663,124
[45] Date of Patent: May 5, 1987

[54] REACTION PRODUCT OF HYDROGEN SULFIDE WITH THE REACTION PRODUCT OF A DIONE AND A PRIMARY POLYAMINE

[75] Inventor: Michael J. Incorvia, Houston, Tex.

[73] Assignee: Texaco, Inc., White Plains, N.Y.

[21] Appl. No.: 771,753

[22] Filed: Sep. 3, 1985

[51] Int. Cl.$^4$ ................ C23F 11/16; C09K 15/26; C09K 15/30

[52] U.S. Cl. ........................... 422/7; 422/16; 106/14.15; 106/14.31; 252/8.555; 252/392; 252/390

[58] Field of Search ........... 252/8.55 E, 390, 392; 106/14.15, 14.31; 422/16, 7

[56] References Cited

U.S. PATENT DOCUMENTS

| | | | |
|---|---|---|---|
| 2,466,517 | 4/1949 | Blair, Jr. et al. | 252/8.55 |
| 2,485,309 | 10/1949 | Nunn, Jr. | 252/392 |
| 2,496,354 | 2/1950 | Mayer et al. | 252/8.55 |
| 2,514,508 | 7/1950 | Nunn, Jr. | 252/392 |
| 2,596,273 | 5/1952 | Mayer et al. | 252/8.55 |
| 2,596,425 | 5/1952 | Mayer et al. | 252/8.55 |
| 3,262,791 | 7/1966 | Dickson et al. | 252/392 X |
| 3,448,154 | 6/1969 | Broadhead et al. | 252/392 X |
| 3,449,424 | 6/1969 | Andress, Jr. et al. | 252/392 X |
| 3,712,863 | 1/1973 | Bundrant et al. | 252/8.55 E |
| 3,770,377 | 11/1973 | Scott et al. | 422/12 |
| 3,843,547 | 10/1974 | Kaufman et al. | 252/392 X |
| 3,909,200 | 9/1975 | Redmore | 252/8.55 E X |
| 3,932,296 | 1/1976 | Byth | 252/8.55 E X |
| 4,292,047 | 9/1981 | Vartanian et al. | 252/392 X |
| 4,460,482 | 7/1984 | Wu | 252/8.55 E |

*Primary Examiner*—John F. Terapane
*Assistant Examiner*—Matthew A. Thexton
*Attorney, Agent, or Firm*—Jack H. Park; Kenneth R. Priem; Harold J. Delhommer

[57] ABSTRACT

A series of water-dispersible corrosion inhibiting solutions are disclosed which contain about 10 ppm to about 70% by weight of the reaction product of a dione and a primary polyamine. The use of these reaction products dramatically reduces $H_2S$ and $CO_2$ corrosion rates when used in a continuous treatment of preferbly about 10 ppm to about 250 ppm or when used in a batch filming treatment.

20 Claims, No Drawings

REACTION PRODUCT OF HYDROGEN SULFIDE WITH THE REACTION PRODUCT OF A DIONE AND A PRIMARY POLYAMINE

BACKGROUND OF THE INVENTION

The invention relates to organic inhibitor treating solutions and a method for using such solutions to reduce corrosion from the harsh fluid environments encountered in the oil field. More particularly, the invention concerns treating solutions containing the reaction product of a dione and a primary polyamine. Such solutions are effective in reducing sweet and sour corrosion.

Corrosion that occurs in an oil field environment is extremely complex and tends to attack all manner of metal equipment above and below ground. The principle corrosive agents found in the well fluids include hydrogen sulfide, carbon dioxide, oxygen, organic acids and solubilized salts. These agents may be present individually or in combination with each other. Valves, fittings, tubing, pumps, precipitators, pipelines, sucker rods, and other producing equipment are particularly susceptible. Deposits of rust, scale, corrosion by-products, paraffin and other substances create ideal environments for concentration cells. Carbon dioxide and hydrogen sulfide induced pitting is encouraged by such deposits. Acidic condensate that collects on metal tubing will also cause pitting. Extreme temperatures and pressures in downhole environments further accelerate corrosion.

Very often as oil fields mature and enhanced recovery methods such as water flooding and miscible flooding are instituted, the concentrations of hydrogen sulfide and carbon dioxide in the well fluids increases dramatically. This increase in concentration and the resultant increase in sweet corrosion or sour corrosion may make older oil fields economically unattractive due to excessive corrosion costs.

Amines and ethoxylated amines of various structures have been employed in corrosion inhibition systems. U.S. Pat. No. 2,466,517 provides one example. U.S. Pat. Nos. 2,485,309; 2,496,354; 2,514,508; 2,596,273 and 2,596,425 disclose corrosion control use of reaction products of selected amines and formaldehyde, chiefly methylol melamine.

SUMMARY OF THE INVENTION

A series of water soluble, or at least water-dispersible, corrosion inhibiting solutions are disclosed which contain about 10 ppm to about 70.0 percent by weight of the reaction product of a dione and a primary polyamine. It has been discovered that the use of these reaction products dramatically reduces oil field corrosion rates.

A preferred corrosion inhibiting solution of the invention contains about 10 ppm to about 70 percent by volume of the dione/primary polyamine reaction product in a solvent which may be water, brine, hydrocarbon or a mixture of such solvents. It is preferred that the reaction product be used in a continuous treatment wherein the metal to be protected from corrosion is continuously contacted with about 10 ppm to about 250 ppm of the reaction product. In most cases, the reaction product will be in a water or brine solution. The reaction product, however, can be stored and shipped in solutions with concentrations ranging up to and greater than 70 percent dione/primary polyamine reaction product by volume. The reaction product of the dione and the primary polyamine may also be reacted with hydrogen sulfide to form a derivative which may be as effective at controlling sweet and sour corrosion as the first reaction product. The invention also encompasses solutions containing imines, which are the chief dione/polyamine reaction products.

Metal equipment can be protected through the use of the corrosion inhibiting solutions of the present invention by contacting metal with an effective amount of inhibiting solution containing the dione/primary polyamine reaction product in a continuous exposure treatment or in a batch filming treatment. Solution concentration should be in the range of about 10 ppm to about 250 ppm in a continuous exposure treatment. Higher concentrations should be used in batch filming treatments to create a more durable film.

DETAILED DESCRIPTION

Perhaps the most costly problem in oil field environment is corrosion of piping and equipment due to sweet and sour corrosion. It has been discovered that the additions of small amounts of reaction product of a dione and a primary polyamine effectively inhibits corrosion from both carbon dioxide and hydrogen sulfide.

Although this invention comprises corrosion inhibiting solutions containing about 10 ppm to about 70 percent by volume of the instant reaction product, the reaction product is preferably delivered to the corrosion sites in a continuous treating solution containing about 10 ppm to about 250 ppm of the reaction product. The preferred diones to create the reaction product are diones having about 4 to about 15 carbon atoms. Excellent results have been obtained with butanedione, pentanedione, hexanedione, heptanedione, octanedione and benzil. The most preferred primary polyamines to use in creating the reaction product are primary diamines such as ethylenediamine, diaminopropane, diaminobutane, diaminopentane, diaminohexane, diaminoheptane, and diaminooctane. Alkoxylated diamine and triamine compounds have also functioned well.

When a dione is reacted with a primary polyamine, the reaction product will include several groups of chemical compounds, depending upon the exact reactants. The product reaction mixture may contain one or more of the following compounds: hemiaminals, aminals, enamines and imines. The imines are the primary reaction product of the dione/polyamine reaction. Tests of all four of these compound groups produced from a dione/polyamine reaction have shown all four groups to be somewhat effective in reducing corrosion. The imines and the hemiaminals were generally highly effective in corrosion control. The preferred imines are cyclic compounds having from about five to about twenty-five carbon atoms. When these inhibitor compounds are reacted with gaseous hydrogen sulfide, their inhibiting ability is enhanced in most cases.

The effectiveness of a given organic inhibitor system generally increases with the concentration, but because of cost considerations, most solutions when fully diluted in their working environment must be effective in quantities of less than about 0.01 percent by weight (100 ppm). The invention solution is effective throughout the range of about 10 ppm to about 250 ppm in a continuous injection method, with higher concentrations generally producing greater protection. At concentrations higher than 250 ppm, percent protection may decrease, depending upon the reaction product employed. Although it may not be cost effective, the invention inhibiting solution may be employed in the field with up to about 1 percent by volume of the instant reaction product.

It is desirable to store and transport the invention corrosion solution with a higher dione/primary polyamine reaction product concentration to save volume and shipping costs, such as about 1 percent to about 70 percent by volume, preferably about 15 percent to about 60 percent by volume of the solution. Most of the reaction products of the instant invention are soluble in water, or at least water-dispersible. Some may require a hydrocarbon such as an alcohol mixed with the water solvent to maintain the active ingredient in solution. With only water as a solvent at these higher concentrations, settling problems may occur which would make dilution and use in the field quite difficult.

For example, a drum containing a solution of 25 percent by volume of the instant reaction product and 75 percent solvent may need a solvent system of about 85 percent water and 15 percent alcohol. Practically any alcohol may be used as solvent, but lower molecular weight alcohols are preferred, primarily because of their low costs. Isopropanol is a preferred alcohol solvent because of its costs. Methanol, ethanol, propanol, butanol and pentanol may all be used. Ethylene glycol and propylene glycol are also preferred alcohol solvents because they can be mixed with isopropanol or the other alcohols to lower the flash point and pour point of the solution. Of course, much larger amounts of alcohol may be employed, but water is preferred because of its cost.

Even at higher concentrations, settling should only occur with the reaction products that are not very water soluble, such as Sample 4 in Table 1 prepared from benzil and diaminopropane. 1% Solutions of other invention reaction products in water have endured over one year of shelf life without any settlement. The use of alcohol as part of the solvent should increase the stability of most of these solutions.

The dione and primary polyamine are reacted in the stoichiometric proportions of about 0.7/1 dione to polyamine to about 1.0/0.7 dione to polyamine. The reaction is normally conducted at ambient temperature although the reaction will produce desirable reaction products at an elevated temperature, which may range up to about 150° C. Some of the dione/polyamine reactions are exothermic. The resulting reaction product may be further modified by reacting the reaction product in a hydrogen sulfide atmosphere at an elevated temperature, such as about 100° C. to about 160° C. Any unreacted hydrogen sulfide is removed from the system after reaction.

The corrosion inhibiting solutions of the invention which contain the instant reaction product may be employed in different locations in the oil field. Since the solutions offer substantial improvement over present inhibitor systems, they may be used to protect downhole piping and equipment in applications such as subsurface water injection for pressure maintenance or disposal, or drilling and production applications, as well as in above-ground oil or water flow lines and equipment.

The invention solution may be employed in both general methods of inhibiting solution treatment, continuous injection and batch. In a continuous injection treatment, the active ingredient of the corrosion inhibiting solution is maintained at the required levels of treatment, preferably about 10 ppm to about 250 ppm, in areas where corrosive fluids contact the metallic parts desired to be protected.

However, in batch applications, the thick filming formulation in an aromatic hydrocarbon solvent is preferred. Either method, continuous injection or batch, permits the inhibitor solution to contact the metal to be protected and form an organic barrier over the metal.

If a batch method is employed, a slug of inhibiting solution containing the instant reaction product should be injected into a closed system with a concentration of about 0.1% to about 25% by volume, preferably about 5% to about 15% inhibiting solution in diluent. The diluted inhibiting solution should be allowed to remain in contact with the metal to be protected for sufficient time to form a durable film. The contact time period is preferably at least 12 hours, most preferably at least 24 hours. Afterwards, normal production or flow of fluids should be resumed, flushing out excess inhibitor solution. The batch treatment should be repeated when necessary to maintain film durability over the metal to be protected, preferably not more often than quarterly.

Surfactants may also be added to the novel inhibiting solutions to increase dispersion and filming. However, increased surfactant quantities may also decrease performance of the overall corrosion inhibiting solution.

At present, an industry established procedure for testing oil field corrosion inhibitors does not exist. Because of widely varying corrosion conditions in the oil field, it is impractical to establish a universal standard laboratory test. But it is desirable to have tests that are easily duplicated and can approximate the continuous type of liquid and gas exposure that occurs in wells and flow lines in the oil field. One test simulating field usage has achieved some following in the industry. The continuous exposure procedure set forth in January 1968 issue of "Material Protections" at pages 34–35 was followed to test the subject invention. The test offers an excellent indication of the ability of corrosion inhibitors to protect metals immersed in either sweet or sour fluids.

The following examples will further illustrate the novel corrosion treating solutions of the present invention containing said reaction product. These examples are given by way of illustration and not as limitations on the scope of the invention. Thus, it should be understood that materials present in the corrosion treating solutions may be varied to achieve similar results within the scope of the invention.

EXAMPLES

General Test Procedure

The metal specimens were immersed in sweet or sour fluid environments for seventy-two (72) hours to approximate continuous exposure conditions in the oil field. The sweet fluid test environment was established by gassing the test solution with carbon dioxide. A sour fluid test environment was created by bubbling hydrogen sulfide through the test solution. The specimens were tested in both carbon dioxide and hydrogen sulfide environments with and without the claimed reaction product.

The metal test specimens were cold-rolled, mild steel coupons which measured 3 inches by 0.5 inches by 0.005 inches. These coupons were initially cleaned in order to remove any surface film, dried and then weighed.

Four ounce glass bottles were filled with two types of test solutions. The first simulated an oil-brine environment and consisted of 10 milliliters of Texaco EDM fluid, a Texaco trademarked lube oil cut having an API gravity of about 39°, 90 milliliters of a 10% synthetic brine and 1 milliliter of dilute (6%) acetic acid. The synthetic brine contained 10% sodium chloride and 0.5% calcium chloride by weight. The second test solution simulated a brine environment and was composed of 100 milliliters of the same 10% synthetic brine and 1 milliliter of dilute acetic acid. The oil-brine and brine test solutions were then gassed for 5 to 10 minutes with carbon dioxide to create a sweet test environment or hydrogen sulfide to create a sour test environment. The solution gassing was designed to remove any dissolved oxygen as well as create the sweet or sour environment. Next, a measured concentration of the reaction product was placed in the bottles.

The steel test coupons were then placed within the bottles. The bottles were capped and mounted on the spokes of a 23 inch diameter, vertically mounted wheel and rotated for 72 hours at 30 rpm inside an oven maintained at 160° F. for $CO_2$ and 120° F. for $H_2S$. The coupons were removed from the bottles, washed and scrubbed with dilute acid for cleaning purposes, dried and weighed. The corrosion rate in mils per year (mpy) was then calculated from the weight loss. One mpy is equivalent to 0.001 inches of metal lost per year to corrosion. Additionally, the test coupons were visually inspected for the type of corrosive attack, e.g., hydrogen blistering, pitting and crevice corrosion or general corrosion.

All sample reaction products were prepared at ambient temperature. Some of the reactions were exothermic. After reaction occurred, all samples were aged overnight for about 16 to 20 hours at 100° C. to make sure the reaction was driven to completion.

For the corrosion protecting tests, most of the reaction product samples were tested in a solvent of an aromatic hydrocarbon cut sold under the trademark TAS by Texaco Chemical Company. This was the solvent used for all tests except those which state "$H_2S$ Derivative in Water." In those cases, water was the only solvent. The 20% and 90% Water-Cut tests were run in an environment of 20% and 90% brine with Texaco EDM fluid making up the remainder.

Jeffamine D-400 is a trademarked di-functional polyoxypropyleneamine sold by Texaco Chemical Company having an average molecular weight of about 400. Jeffamine ED-900 is a trademarked di-functional polyoxyalkleneamine sold by Texaco Chemical Company having an average molecular weight of about 900. Jeffamine T-403 is a trademarked tri-functional polyoxypropyleneamine sold by Texaco Chemical Company with an average molecular weight of about 400.

Reference to the continuous filming test results of Tables 1 and 2 indicate that every reaction product gave excellent results (>90%) for $H_2S$ control in at least one environment. Most reaction products gave excellent $H_2S$ results in two or three of the three different environments. Excellent results for $CO_2$ control (>80%) were a little harder to achieve, but were obtained by the majority of the samples tested. Sample 1 and the $H_2S$ derivative of Sample 1 in TAS gave the best overall results for all environments. Sample 6, a hemiaminal isolated from Sample 1 gave very good results in the 90% water cut environment. Jeffamine T-403 was also tested and gave good to excellent results for $H_2S$ control and some excellent results for $CO_2$ control.

Many other variations and modifications may be made in the concepts described above by those skilled in the art without departing from the concepts of the present invention. Accordingly, it should be clearly understood that the concepts disclosed in the description are illustrative only and are not intended as limitations on the scope of the invention.

TABLE 1

Percent Protection Afforded Under Continuous Filming Standard Wheel Test with 25 ppm of Inhibitor

| INHIBITOR | 20% WATER-CUT $CO_2$ | 20% WATER-CUT $H_2S$ | 90% WATER-CUT $CO_2$ | 90% WATER-CUT $H_2S$ | 100% WATER-CUT $CO_2$ | 100% WATER-CUT $H_2S$ |
|---|---|---|---|---|---|---|
| Sample 1 | 92% | 89% | 97% | 96% | 72% | 95% |
| $H_2S$ Derivative of Sample 1 | 80% | 97% | 96% | 96% | 98% | 93% |
| $H_2S$ Derivative in Water | 60% | 76% | 86% | 98% | 87% | 93% |
| Sample 2 | 53% | 91% | 82% | 98% | 84% | 87% |
| $H_2S$ Derivative of Sample 2 | 74% | 96% | 92% | 98% | 85% | 93% |
| $H_2S$ Derivative in Water | 63% | 76% | 82% | 98% | 68% | 87% |
| Sample 3 | 65% | 82% | 86% | 96% | 69% | 89% |
| $H_2S$ Derivative of Sample 3 | 81% | 96% | 91% | 97% | 84% | 97% |
| Sample 4 | 83% | 95% | 94% | 97% | 67% | 94% |
| $H_2S$ Derivative of Sample 4 | — | 94% | 95% | 97% | 89% | 96% |
| Sample 5 | 68% | 82% | 88% | 98% | 64% | 91% |
| $H_2S$ Derivative of Sample 5 | 79% | 97% | 90% | 98% | 69% | 89% |
| $H_2S$ Derivative in Water | 45% | 72% | 78% | 97% | 26% | 88% |
| Sample 6 | 74% | 79% | 93% | 96% | 79% | 85% |

Sample 1: 2,5-Hexanedione and 1,8-Diaminooctane
Sample 2: 2,3-Butanedione and Jeffamine D-400
Sample 3: 2,4-Pentanedione and 1,7-Diaminoheptane
Sample 4: Benzil and 1,3-Diaminopropane
Sample 5: 2,5-Hexanedione and Ethylenediamine
Sample 6: 2,5-Dimethyl-2,5-diol-1,6-Diazacyclotetradecane isolated from the reaction product of Sample 1.

TABLE 2

Percent Protection Under Continuous Filming Standard Wheel Test

| | 90% WATER-CUT $CO_2$ | 90% WATER-CUT $H_2S$ | 100% WATER-CUT $CO_2$ | 100% WATER-CUT $H_2S$ |
|---|---|---|---|---|
| Sample 1 (1000 ppm) | 86% | 94% | 85% | 92% |
| $H_2S$ Derivative of Sample 1 (50 ppm) | 99% | 93% | 97% | 92% |
| Sample 5 (1000 ppm) | 0% | 100% | 0% | 94% |
| $H_2S$ Derivative of Sample 5 (38 ppm) | 97% | 98% | 95% | 91% |
| Sample 7 (1000 ppm) | 65% | 94% | 38% | 95% |
| $H_2S$ Derivative of Sample 7 (47 ppm) | 96% | 98% | 80% | 86% |
| Sample 8 (1000 ppm) | 0% | 94% | 0% | 90% |
| $H_2S$ Derivative of Sample 8 (25 ppm) | 71% | 78% | 65% | 94% |
| Sample 9 (1000 ppm) | 0% | 81% | 0% | 79% |
| $H_2S$ Derivative of Sample 9 (25 ppm) | 68% | 77% | 57% | 92% |

Sample 1: 2,5-Hexanedione and 1,8-Diaminooctane
Sample 5: 2,5-Hexanedione and Ethylenediamine
Sample 7: 2,5-Hexanedione and Jeffamine D-400
Sample 8: 2,4-Pentanedione and 1,2-Diaminopropane
Sample 9: 2,3-Butanedione and Jeffamine ED-900

What is claimed is:
1. A water-dispersible corrosion inhibiting solution, comprising:
a solvent; and about 10 ppm to about 1.0% by weight of a second reaction product of hydrogen sulfide and a first reaction product, said first reaction product formed by the reaction of a dione and a primary polyamine.

2. The corrosion inhibiting solution of claim 1, wherein the solvent is water.

3. The corrosion inhibiting solution of claim 1, wherein the solvent is brine.

4. The corrosion inhibiting solution of claim 1, wherein the solvent is a hydrocarbon.

5. The corrosion inhibiting solution of claim 1, wherein the solvent is a hydrocarbon and brine mixture.

6. The corrosion inhibiting solution of claim 1, wherein the hydrogen sulfide and the first reaction product are reacted together at an elevated temperature of about 100° C. to about 160° C.

7. The corrosion inhibiting solution of claim 1, wherein the primary polyamine is a diamine.

8. The corrosion inhibiting solution of claim 1, wherein the primary polyamine is a triamine.

9. The corrosion inhibiting solution of claim 1, wherein the dione has about 4 to about 15 carbon atoms.

10. The corrosion inhibiting solution of claim 1, wherein said dione and primary polyamine are reacted in the proportions of about 0.7/1 dione to polyamine to about 1/0.7 dione to polyamine.

11. The corrosion inhibiting solution of claim 1, wherein all unreacted hydrogen sulfide is removed from the second reaction product mixture.

12. The corrosion inhibiting solution of claim 1, wherein the concentration of said second reaction product is about 20 ppm to about 250 ppm.

13. A water-dispersible corrosion inhibiting solution, comprising:
about 0% to about 99% by volume of water;
about 0% to about 99% by volume of an alcohol; and
about 1% to about 70% by volume of a second reaction product of hydrogen sulfide and a first reaction product, said first reaction product formed by the reaction of a dione and a primary polyamine.

14. The corrosion inhibiting solution of claim 13, wherein water comprises about 30% to about 70% by volume of the solution, alcohol comprises about 0% to about 25% by volume of the solution and said second reaction product comprises about 15% to about 60% by volume of the solution.

15. The corrosion inhibiting solution of claim 13, wherein the alcohol is selected from the group of alcohols consisting of methanol, ethanol, propanol, butanol, pentanol, ethylene glycol, propylene glycol and mixtures thereof.

16. A water-dispersible corrosion inhibiting solution, comprising:
a solvent; and
about 10 ppm to about 1% by weight of a reaction product of hydrogen sulfide and an imine.

17. A method of protecting metals from corrosive agents in hydrocarbon and aqueous fluids which comprises contacting metal with an effective amount of a second reaction product of hydrogen sulfide and a first reaction product, said first reaction product formed by the reaction of a dione and a primary polyamine.

18. The method of claim 17, wherein said reaction product is mixed with fluids so that a concentration of about 5 ppm to about 250 ppm of said second reaction product continuously contacts the metal.

19. The method of claim 17, further including the steps of:
contacting the metal to be protected with said second reaction product in a concentration of about 0.1% to about 25% by volume of said second reactron product in a solvent for a time sufficient to form a durable film over the surface of the metal; and
repeating the film-forming metal contact treatment when necessary to maintain the film.

20. A water-dispersible corrosion inhibiting solution, comprising:
a solvent; and
about 20 ppm to about 250 ppm of a second reaction product of hydrogen sulfide and a first reaction product, said first reaction product formed by the reaction of a primary diamine with a dione having about 4 to about 15 carbon atoms,
said second reaction product prepared at an elevated temperature of about 100° C. to about 160° C., and having all unreacted hydrogen sulfide removed from the second reaction product mixture.

* * * * *